(12) United States Patent
Pittaway et al.

(10) Patent No.: US 7,066,177 B2
(45) Date of Patent: Jun. 27, 2006

(54) EXHALATION VALVES

(75) Inventors: Alan Kenneth Pittaway, Buckinghamshire (GB); Surinderjit Kumar Jassell, Middlesex (GB)

(73) Assignee: Intersurgical Limited, Berkshire (GB)

( * ) Notice: Subject to any disclaimer, the term of this patent is extended or adjusted under 35 U.S.C. 154(b) by 0 days.

(21) Appl. No.: 10/900,477

(22) Filed: Jul. 28, 2004

(65) Prior Publication Data

US 2005/0034726 A1 Feb. 17, 2005

(30) Foreign Application Priority Data

Jul. 30, 2003 (GB) ................... 0317801.9

(51) Int. Cl.
*A62B 9/02* (2006.01)

(52) U.S. Cl. .................... 128/205.24; 128/201.28; 128/205.16

(58) Field of Classification Search ........... 128/201.28, 128/203.11, 204.18, 205.15, 205.16, 205.24, 128/206.15, 207, 207.16, 207.12; 251/61.1, 251/82; 137/529, 542

See application file for complete search history.

(56) References Cited

U.S. PATENT DOCUMENTS

| | | | | |
|---|---|---|---|---|
| 2,583,502 A | * | 1/1952 | Wiggins | 137/81.1 |
| 3,643,686 A | * | 2/1972 | Koegel | 137/512 |
| 3,688,794 A | * | 9/1972 | Bird et al. | 137/529 |
| 3,874,379 A | | 4/1975 | Enfield et al. | |
| 3,933,171 A | | 1/1976 | Hay | |
| 4,239,038 A | * | 12/1980 | Holmes | 128/205.13 |
| 4,241,756 A | * | 12/1980 | Bennett et al. | 137/496 |
| 4,298,023 A | * | 11/1981 | McGinnis | 137/529 |
| 4,374,521 A | * | 2/1983 | Nelson et al. | 128/205.13 |
| 4,454,893 A | | 6/1984 | Orchard | |
| 4,463,755 A | | 8/1984 | Suzuki | |
| 4,624,442 A | * | 11/1986 | Duffy et al. | 251/61.1 |
| 4,648,394 A | * | 3/1987 | Wise | 128/201.24 |
| 4,694,825 A | * | 9/1987 | Slemmer et al. | 128/205.24 |
| RE32,553 E | * | 12/1987 | Bennett et al. | 137/271 |
| 4,712,580 A | * | 12/1987 | Gilman et al. | 137/512.15 |
| 4,774,941 A | * | 10/1988 | Cook | 128/205.13 |
| 5,020,532 A | * | 6/1991 | Mahoney et al. | 128/205.24 |
| 5,063,925 A | | 11/1991 | Frank et al. | |
| 5,127,400 A | * | 7/1992 | DeVries et al. | 128/205.24 |
| 5,184,609 A | * | 2/1993 | Hart | 128/205.24 |
| 5,722,394 A | * | 3/1998 | Loescher | 128/205.24 |
| 5,746,199 A | * | 5/1998 | Bayron et al. | 128/205.24 |
| 5,906,203 A | * | 5/1999 | Klockseth et al. | 128/205.24 |

(Continued)

FOREIGN PATENT DOCUMENTS

EP 0 143 618 B1 6/1985

(Continued)

*Primary Examiner*—Henry Bennett
*Assistant Examiner*—Shumaya B. Ali
(74) *Attorney, Agent, or Firm*—Nixon Peabody LLP

(57) ABSTRACT

An exhalation valve (10) is disclosed for use with an exhalation port (14) of a respiratory circuit. The exhalation valve comprises a hermetically sealed gas chamber (20,120), a gas inlet (22,122) for supplying gas to the gas chamber, and a membrane (24,124) of flexible material that defines at least part of a wall of the gas chamber. The membrane is deformable by a change in the pressure differential between the gas within the gas chamber and the gas within the exhalation port between an inoperative configuration and an operative configuration in which the membrane restricts the flow of gas from the exhalation port to a greater extent than in said inoperative configuration. The membrane is inherently planar but is mounted within the exhalation valve such that deformation of the membrane to its operative configuration occurs substantially without increase of the surface area of the membrane.

37 Claims, 4 Drawing Sheets

U.S. PATENT DOCUMENTS

| | | | |
|---|---|---|---|
| 6,098,622 A * | 8/2000 | Nobile et al. | 128/205.24 |
| 6,250,329 B1 * | 6/2001 | Rashidi | 137/467 |
| 6,253,764 B1 | 7/2001 | Calluaud | |
| 6,371,117 B1 * | 4/2002 | Lindqvist et al. | 128/207.12 |
| 6,415,793 B1 * | 7/2002 | Kretz | 128/205.24 |
| 6,634,357 B1 * | 10/2003 | Hamilton | 128/205.24 |
| 2002/0056826 A1 * | 5/2002 | Tripoli | 251/331 |
| 2003/0029448 A1 * | 2/2003 | Swetish | 128/201.11 |
| 2003/0066527 A1 * | 4/2003 | Chen | 128/204.18 |

FOREIGN PATENT DOCUMENTS

| | | |
|---|---|---|
| FR | 2 535 612 A1 | 5/1984 |
| FR | 2 784 587 A1 | 4/2000 |
| WO | WO 00/45883 A1 | 8/2000 |

\* cited by examiner

EXHALATION VALVES

This application claims the priority benefit of UK patent application 0317801.9, filed Jul. 30, 2003, which is hereby incorporated by reference in its entirety.

BACKGROUND OF THE INVENTION

This invention relates to exhalation valves used where Patient End Expiratory Pressure (PEEP) is applied to an artificial respiratory circuit, and in particular to exhalation valves used where the applied Patient End Expiratory Pressure is adjustable.

When a patient is unable to breathe unaided, or requires assistance with breathing, the patient is usually connected to an artificial respiratory circuit including a ventilator programmed by a clinician to deliver an appropriate volume of air, or an air/oxygen mixture, to the patient. In such a respiratory circuit, it is desirable to prevent the patient from exhaling fully, and therefore the patient's lungs from deflating fully. This is because complete deflation, and subsequent reflation, of the patient's lungs requires a significant amount of the patient's energy.

Prevention of total exhalation is generally achieved by including a mechanism in the respiratory circuit which only allows exhaled breath above an appropriate exhalation pressure to escape the respiratory circuit through an exhalation port. Prevention of total exhalation in this way is known as applying "PEEP" to the respiratory circuit, where "PEEP" refers to Patient End Expiratory Pressure.

PEEP is currently applied to a respiratory circuit using either a so-called PEEP valve or an exhalation valve to control the passage of the exhaled breath through an exhalation port. A PEEP valve has a fixed and pre-determined release pressure for the exhalation port. An exhalation valve has a release pressure that is determined by the pressure of a gas within the hermetically sealed exhalation valve. This gas within the exhalation valve is usually supplied by the ventilator at a pressure that is determined and selected by a clinician.

Conventionally, exhalation valves comprise a chamber that is supplied by the ventilator, during use, with a gas under pressure, and a flexible membrane which defines a wall of the chamber and is disposed, in its relaxed state, slightly above the exhalation port of the respiratory circuit. In use, gas with a pressure selected by the user is supplied to the chamber by the ventilator. The supplied gas deforms the membrane elastically and outwardly from the chamber and into engagement with the exhalation port, thereby sealing the exhalation port. Therefore, in theory, the pressure of the exhaled gas within the respiratory circuit must exceed the pressure of the gas within the exhalation valve for the exhaled gas to be able to escape the respiratory circuit through the exhalation port. In this way, the pressure of the gas within the exhalation valve, which is determined and selected by a clinician, should equal the positive end expiratory pressure applied to the respiratory circuit by the exhalation valve.

Conventional membranes are usually formed in an elastomeric material, such as silicone rubber. There are a variety of different shapes of membrane currently in use, including a membrane having a generally top-hat shape where the central flat circular wall of the membrane is elastically deformable into engagement with the exhalation port, and a membrane having the form of a balloon where the membrane is elastically inflatable into engagement with the exhalation port.

However, a problem with exhalation valves of this type is that a certain amount of pressure, the "deforming pressure", is required to elastically deform the membrane into engagement with the exhalation port. The PEEP applied to the respiratory circuit using conventional exhalation valves is not therefore the pressure of the gas within the exhalation valve. Instead, the PEEP applied to the respiratory circuit using conventional exhalation valves is equal to the pressure of the gas within the exhalation valve minus the deforming pressure. For example, a selected pressure of 10 cm $H_2O$ for the exhalation valve gas can deliver a PEEP as low as 8 cm $H_2O$.

In order to address this problem, ventilators have been developed that include microprocessor controlled feedback for the pressure line to the exhalation valve so that this loss of pressure is automatically compensated for by increasing the pressure within the exhalation valve. However, such solutions are very expensive and require the ventilator, which is an expensive piece of equipment, to be replaced in order to solve the problem. For this reason, only a very small proportion of ventilators currently in everyday clinical use include a compensating pressure feedback mechanism, as discussed above.

There has now been devised an improved exhalation valve which overcomes or substantially mitigates the above-mentioned and/or other disadvantages associated with the prior art.

SUMMARY OF THE INVENTION

According to the invention, there is provided an exhalation valve for use with an exhalation port of a respiratory circuit, the exhalation valve comprising a hermetically sealed gas chamber, a gas inlet for supplying gas to the gas chamber, and a membrane of flexible material defining at least part of a wall of the gas chamber, the membrane being situated, in use, adjacent to the exhalation port, and the membrane being deformable by a change in the pressure differential between the gas within the gas chamber and the gas within the exhalation port between an inoperative configuration and an operative configuration in which the membrane restricts the flow of gas from the exhalation port to a greater extent than in said inoperative configuration, wherein the membrane is inherently planar but is mounted within the exhalation valve such that deformation of the membrane to its operative configuration occurs substantially without increase of the surface area of the membrane.

The exhalation valve according to the invention is advantageous principally because the pressure differential required to deform the membrane from its inoperative configuration to its operative configuration, and hence increase the restriction of the gas flowing out of the exhalation port, in use, is significantly reduced. This is because such deformation involves no, or only minimal, stretching of the membrane, unlike the equivalent deformation in conventional exhalation valves. Therefore, in use, the pressure of the gas within the gas chamber is in significantly closer agreement with the positive end expiratory pressure applied to the respiratory circuit at the exhalation port than has hitherto been possible with conventional exhalation valves. The present invention is also advantageous over conventional exhalation valves because the membrane can be manufactured as a simple disc, which is cheaper to manufacture than many of the membranes used in conventional exhalation valves. In addition, the invention provides a far cheaper and simpler alternative to a ventilator that incorporates a pressure feedback mechanism.

The membrane may either partially or completely occlude an exit opening of the exhalation port in its operative configuration. Where the membrane completely occludes the exit opening, flow of gas from the exhalation port is prevented.

The membrane may be an oversized membrane, ie a membrane that is sized such that the surface area of that part of the membrane that spans a space within which it is held is greater than the cross-sectional area of that space. Where the operative form of the membrane completely occludes an exit opening of the exhalation port, the surface area of that part of the membrane that occludes the exit opening is preferably greater than the cross-sectional area of the exit opening.

In its inoperative configuration, the membrane is therefore preferably convoluted. The convoluted form of the membrane will generally be a form in which the membrane is disposed substantially in a plane, but with corrugations, furrows, wrinkles or ridges such that the membrane has peaks and troughs that extend either side of the plane. The pressure differential required to deform the membrane from its inoperative, convoluted configuration to its operative configuration is significantly reduced in this case because such deformation only requires the membrane to adopt a more regular, generally dome-shaped, form, and therefore no, or only minimal, stretching of the membrane occurs.

The gas chamber is preferably defined by at least two cooperating components and the membrane of flexible material. The two cooperating components preferably engage one another and clamp the inherently planar membrane therebetween (so constituting the mounting) so that the membrane defines at least part of a wall of the gas chamber.

The two cooperating components are preferably adapted to engage one another, and clamp the inherently planar membrane therebetween, along a closed and generally circumferential path. The clamping engagement between the two cooperating components is preferably by means of a closed, and most preferably annular, ridge formed on a first component adapted to engage a circumferential, and most preferably annular, groove formed on a second component.

Preferably, one of the two cooperating components, the sealing component, includes an opening over which the membrane extends so as to define at least a part of a wall of the gas chamber. Most preferably, the sealing component includes an upstanding peripheral skirt adapted to engage with the other cooperating component so as to define the gas chamber. The membrane is preferably formed with planar dimensions larger than those of the area defined by the internal surface of the upstanding peripheral skirt so that when the membrane is positioned across the opening of the sealing component, the membrane abuts the internal surface of the upstanding skirt and is deformed into its inoperative and convoluted configuration. Most preferably, the sealing component has the general form of an annulus and the membrane is a circular disc of flexible material. Engagement of the two cooperating components preferably clamps the membrane in place. Once the membrane has been clamped in place, the two cooperating components are preferably permanently fixed together, most preferably by welding.

The gas chamber is preferably generally cylindrical in form, and preferably has a diameter that is greater than it height. In this case, the membrane preferably forms at least part of an end wall, which is preferably circular in shape, of the cylindrical gas chamber. Most preferably, the membrane defines the majority of an end wall of the gas chamber.

The membrane is preferably manufactured in an inherently smooth and planar form. Preferably, the membrane is a sheet of flexible material. The membrane may be formed directly by injection moulding, or may be cut from a larger sheet of flexible material. The flexible material may be any suitable material that is impermeable to the gas which is supplied to the gas chamber. Most preferably, the flexible material is silicone rubber, or a material with similar properties to silicone rubber. The membrane is most preferably manufactured as a smooth, planar and circular disc of flexible material.

Deformation of the membrane from its inoperative configuration to its operative configuration preferably causes at least part of the membrane to be moved towards the exhalation port. Most preferably, the operative configuration of the membrane either partially or completely occludes an exit opening of the exhalation port, and hence either partially or completely closes the exhalation port, and prevents or inhibits escape of a patient's exhaled breath, which is at a pressure below a threshold pressure, from the respiratory circuit. Most preferably, if the patient's exhaled breath is at a pressure above the threshold pressure, the exhaled breath deforms the membrane away from the exhalation port and escapes from the respiratory circuit. The threshold pressure is substantially equivalent to the positive end expiratory pressure applied to the respiratory circuit at the exhalation port.

Since deformation of the membrane from its inoperative configuration to its operative configuration occurs substantially without increase of the surface area of the membrane, the pressure of the gas within the gas chamber is in significantly closer agreement with the positive end expiratory pressure applied to the respiratory circuit at the exhalation port than has hitherto been possible with conventional exhalation valves. The exhalation valve is most preferably arranged such that the positive end expiratory pressure is substantially equal to the pressure of the gas within the gas chamber.

It will be appreciated that the membrane may move from the inoperative, convoluted configuration to the operative configuration inelastically, in which case there will be no change in the surface area of the membrane. Alternatively, however, where the membrane is elastically deformable, a degree of stretching of the membrane may occur. However, such stretching will generally be slight.

The exhalation valve may be arranged such that before the gas inlet is connected to a supply of gas, and hence the pressure differential is zero, the membrane adopts its inoperative configuration. However, in preferred embodiments, the exhalation valve is arranged such that before the gas inlet is connected to a supply of gas, and hence the pressure differential is zero, the membrane adopts its operative configuration. In this case, the exhalation valve preferably includes resilient means that bias the membrane towards its operative configuration. For example, the resilient means may take the form of a spring that is located within the gas chamber, and acts between the membrane and an opposing wall of the gas chamber.

The presence of such resilient means reduces the time taken for the membrane to be deformed from its inoperative configuration to its operative configuration, and hence either partially or completely close the exhalation port, when the pressure within the exhalation port has dropped below the threshold pressure. This reduction of the time taken to either partially or completely close the exhalation port reduces the amount of breathing gas that escapes through the exhalation valve during closure, and hence increases the amount of breathing gas that is delivered to the patient.

The gas inlet is preferably a tubular gas passageway extending from a wall of the gas chamber. The gas inlet is preferably connected, in use, to a supply of gas which is most preferably provided by a ventilator.

The exhalation valve preferably includes the exhalation port which is adapted to be connected, in fluid communication, to a respiratory circuit. In this way, the membrane can be disposed appropriately relative to the exhalation valve during manufacture. Most preferably, the exhalation valve includes a section of tubing that is adapted to be connected into a respiratory circuit, and the exhalation port branches from the section of tubing.

Preferably, the exhalation port terminates at an exit opening, which is preferably circular in shape, through which exhaled breath from a patient can escape from the respiratory circuit. The membrane may be disposed in any orientation suitable for partially or completely occluding the exit opening. However, the membrane is most preferably disposed parallel to, and above, the exit opening so that the operative form of the membrane occludes the exit opening completely.

The exhalation valve preferably forms part of an otherwise conventional artificial respiratory circuit including a ventilator.

BRIEF DESCRIPTION OF THE DRAWINGS

The invention will now be described in greater detail, by way of illustration only, with reference to the accompanying drawings, in which.

DETAILED DESCRIPTION OF THE INVENTION

Figure 1:
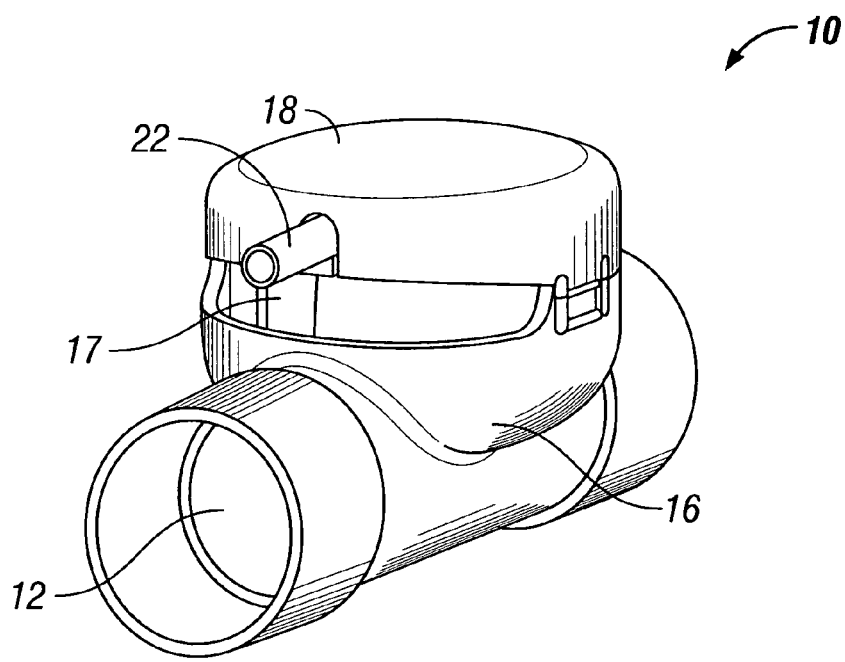
FIG. 1 is a front perspective view of an exhalation valve according to the invention.
Figure 2:
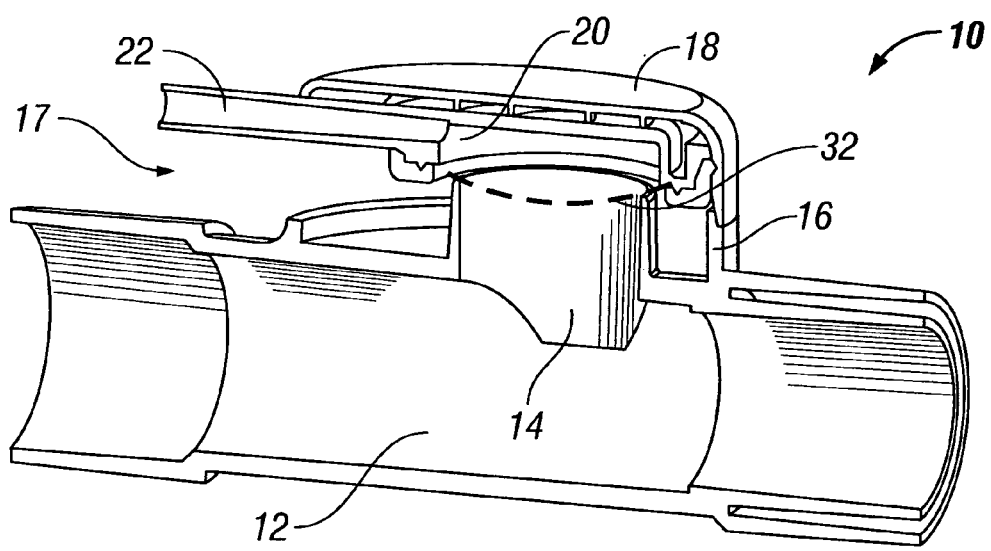
FIG. 2 is a perspective view, from above and to one side, of a longitudinal section through the exhalation valve.
Figure 3:
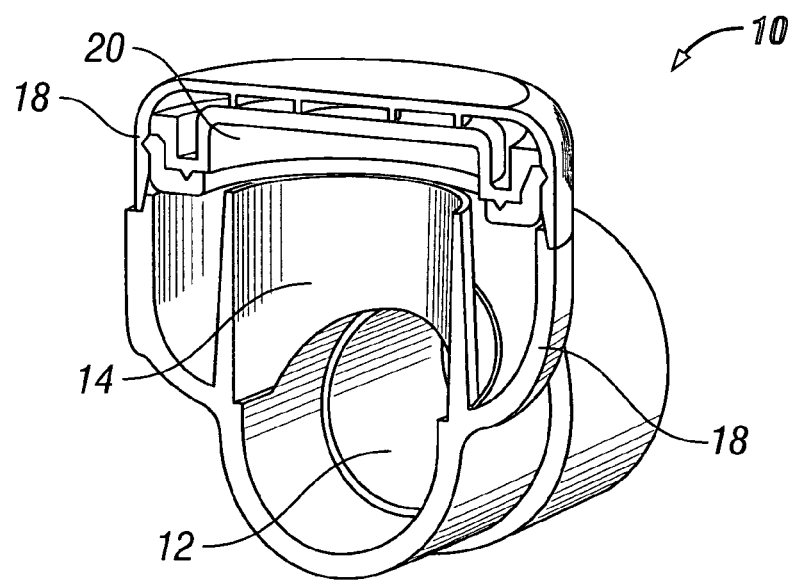
FIG. 3 is a perspective view of a lateral section through the exhalation valve.

FIGS. 1, 2 and 3 show an exhalation valve according to the invention which is generally designated 10. The exhalation valve 10 comprises a respiratory passageway 12, an exhalation port 14, a lower housing 16, an upper housing 18, a gas chamber 20, a gas inlet pipe 22 and a membrane of flexible material 24 (the membrane 24 is not visible in FIG. 1, and is not shown in FIG. 2 or 3, but its location during use is indicated by a broken line 32 in FIG. 2).

The respiratory passageway 12 is adapted at either end to connect to a respiratory circuit. The exhalation port 14 branches perpendicularly from a central portion of the respiratory passageway 12 and terminates at a circular opening. The lower housing 16 has the form of an upright bowl and extends upwardly, around the exhalation port 14, from the upper surface of the respiratory passageway 12. The respiratory passageway 12, the exhalation port 14 and the lower housing 16 are integrally formed as a single component of plastics material by injection moulding. The upper housing 18 is a separate component of plastics material and has the form of an inverted bowl with a side opening for accommodating the gas inlet pipe 22. The upper and lower housings 18,16 are adapted to releasably engage one another and together define an enclosure around the exhalation port 14 and an opening 17 into said enclosure.

The gas chamber 20, gas inlet pipe 22 and membrane 24 all form part of a gas chamber component which is described in more detail below in relation to FIGS. 4, 5 and 6.

Figure 4:
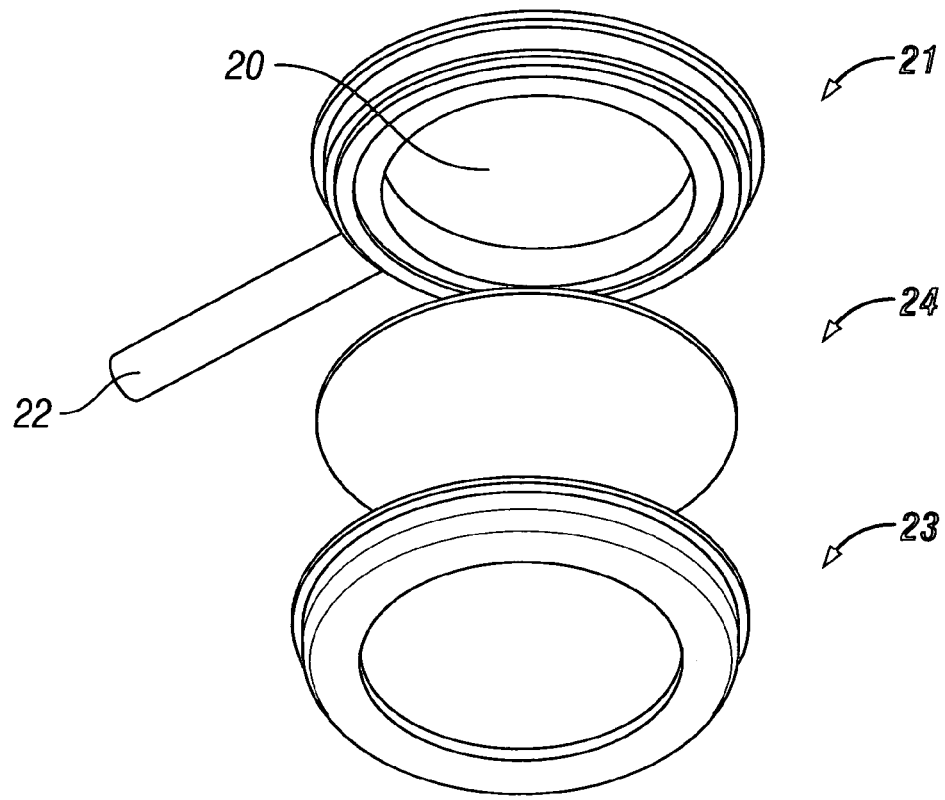
FIG. 4 is an exploded perspective view, from below, of a gas chamber component of the exhalation valve.

FIG. 4 shows an exploded perspective view, from below, of the gas chamber component. The gas chamber component comprises a main body 21, a membrane of flexible material 24, and a sealing ring 23. As viewed in FIG. 4, the main body 21 comprises a circular upper wall and a downwardly extending cylindrical side wall, which together with the membrane 24 define the gas chamber 20. The side wall of the main body 21 is of double-walled construction with an open upper end and a closed lower end, as shown more clearly in FIG. 6. The inwardly facing external surface of the side wall of the main body 21 also includes an opening from which the gas inlet pipe 22 extends.

The sealing ring 23 comprises a generally flat annulus, which defines a central circular opening, and an upstanding skirt at the periphery of the annulus. The upstanding skirt of the sealing ring 23 fits closely around the outermost surface of the side wall of the main body 21. The outermost surface of the upstanding skirt of the sealing ring 23 includes an outwardly extending annular projection that engages with a corresponding annular recess in the internal surface of the upper housing 18. The gas chamber component therefore engages the interior of the upper housing 18 with a snap fit. In addition, the lowermost surface of the side wall of the main body 21 includes a downwardly extending annular ridge which is adapted to engage with an annular groove formed in the upper surface of the annulus of the sealing ring 23.

The main body 21 and sealing ring 23 are injection moulded in plastics material. The membrane 24 is formed as a flat disc of silicone rubber having a diameter that is slightly larger than the circular area defined by the internal surface of the upstanding skirt of the sealing ring 23.

The gas chamber component is formed by first forming the main body 21, the membrane 24 and the sealing ring 23 as separate components. The membrane 24 is then positioned across the circular opening defined by the annulus of the sealing ring 23, overlying the annular groove, with its peripheral edge abutting the internal surface of the upstanding skirt of the sealing ring 23. Since the membrane 24 has a diameter that is slightly larger than the area defined by the internal surface of the upstanding skirt, the membrane 24 is deformed into a wrinkled form in order to fit within the sealing ring 23.

Figure 5:
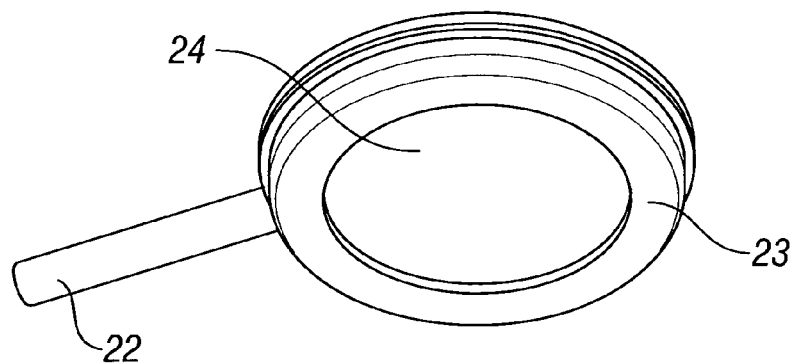
FIG. 5 is a perspective view, from below, of the gas chamber component of the exhalation valve.
Figure 6:
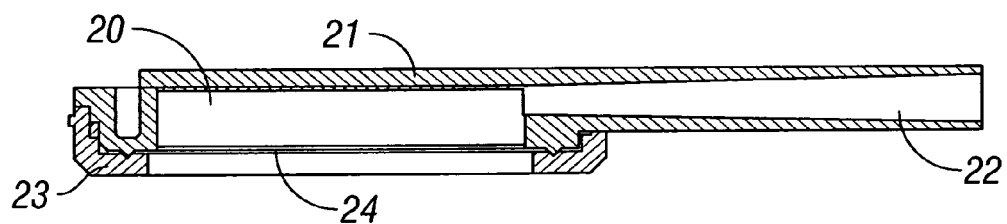
FIG. 6 is a cross-sectional view of the gas chamber component of the exhalation valve.

As shown in FIGS. 5 and 6, the main body 21 and the sealing ring 23 are then engaged and welded together so that the annular ridge of the side wall engages with the annular groove of the annulus with the membrane 24 being clamped therebetween. The membrane 24 is therefore maintained in its wrinkled form by the clamping action of the annular ridge and annular groove.

Turning back to FIGS. 2 and 3, in the assembled exhalation valve, the gas chamber component is engaged with the interior surface of the upper housing 18 with a snap fit. The exhalation valve 10 is arranged such that the gas chamber 20 is disposed within the enclosure defined by the upper and lower housings 18,16 above the exhalation port 14, with the membrane 24 (not shown in FIGS. 2 and 3) disposed slightly above the circular opening of the exhalation port 14.

Figure 7:
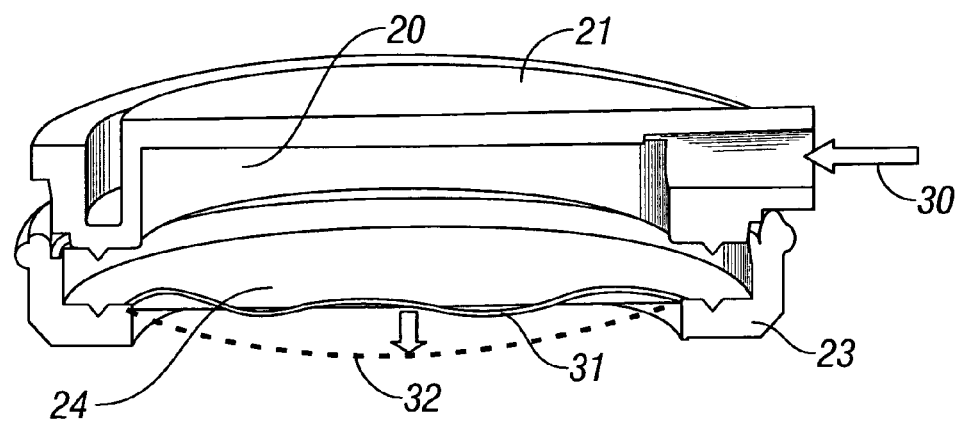
FIG. 7 is a perspective view of a section through the gas chamber component of the exhalation valve, with the components slightly separated, illustrating movement of a membrane during use.

Referring also now to FIG. 7, in use, gas is supplied to the gas chamber 20, under pressure, through the gas inlet pipe 22, as indicated by arrow 30 in FIG. 7. The pressure of the gas supplied to the gas chamber 20 deforms the membrane 24 from its wrinkled form, indicated by the straight line 31 in FIG. 7, to a smooth, dome-shaped form, indicated by the broken lines 32 in FIGS. 2 and 7. This deformation does not involve overall stretching of the membrane 24, as in conventional exhalation valves, but merely involves returning the membrane 24 to its inherently unwrinkled form. Significantly less pressure is therefore required to deform the membrane 24 of the exhalation valve 10 according to the invention compared to the membranes of conventional exhalation valves. The pressure of the gas within the gas chamber 20 is therefore in significantly closer agreement with the nominal patient end expiratory pressure applied to the respiratory circuit than has hitherto been possible with conventional exhalation valves.

The inflated membrane 24 occludes the circular opening of the exhalation port 14 so that the pressure of the exhaled gas within the respiratory passageway 12 and exhalation port 14 must exceed the pressure of the gas within the gas chamber 20 in order for the exhaled gas to pass through the exhalation port 14. If the exhaled gas exceeds this required pressure, the membrane 24 will be deformed away from the exhalation port 14 sufficiently for the exhaled gas to be able to pass through the circular opening of the exhalation port 14, and through the opening 17 in the enclosure formed by the upper and lower housings 18,16.

Figure 8:
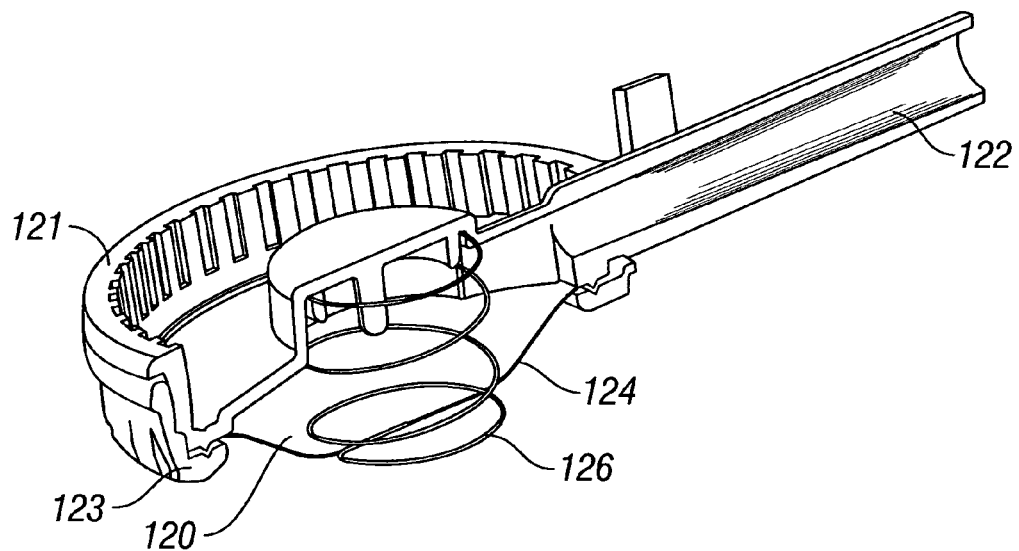
FIG. 8 is a perspective view, from above, of a longitudinal section through an alternative gas chamber component for use with the exhalation valve.
Figure 9:
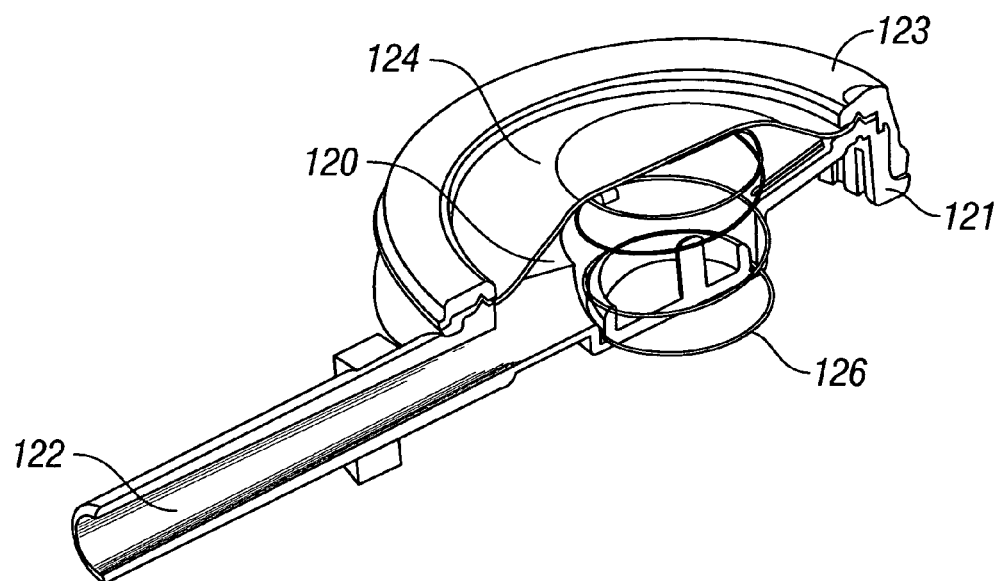
FIG. 9 is a perspective view, from below, of a longitudinal section through the alternative gas chamber component.

FIGS. 8 and 9 show an alternative, and presently preferred, gas chamber component for use with the exhalation valve according to the invention. The alternative gas chamber component shown in FIGS. 8 and 9 is substantially identical to the gas chamber component shown in FIGS. 4 to 7 save that a spring 126 is housed within the gas chamber 120 of the alternative gas chamber component. The main body 121 of the alternative gas chamber component is formed with a cylindrical cavity at the centre of its interior surface that accommodates one end of the spring 126. The other end of the spring 126 abuts an interior surface of the flexible membrane 124.

The flexible membrane 124 is clamped between the main body 121 and the sealing ring 123 of the gas chamber component so that it has a generally planar, wrinkled form, and extends across the opening of the sealing ring 123, in a similar manner to the flexible membrane 24 of the gas chamber component shown in FIGS. 4 to 7. However, the spring 126 acts to deform the flexible membrane 124 from its generally planar, wrinkled form into a smooth, generally dome-shaped form, as shown in FIGS. 8 and 9. The spring 126 has a sufficiently low spring constant so that this deformation does not involve overall stretching of the membrane 124, as in conventional exhalation valves, but merely involves returning the membrane 124 to its inherently unwrinkled form.

In use, gas is supplied to the gas chamber 120, under pressure, through the gas inlet pipe 122, and the membrane 124, which is maintained by the spring 126 in its smooth, generally dome-shaped form, occludes the circular opening of the exhalation port so that the pressure of the exhaled gas within the exhalation port must exceed a threshold pressure in order for the exhaled gas to escape through the exhalation port. The effective pressure exerted by the spring 126 on the flexible membrane 124 is chosen to be as low as possible such that the threshold pressure is approximately equal to the pressure of the gas within the gas chamber 120. If the exhaled gas exceeds this threshold pressure, the membrane 124 will be deformed away from the exhalation port a sufficient amount for the exhaled gas to escape from the exhalation port.

Once the pressure of the exhaled gas within the exhalation port has dropped below the threshold pressure, both the spring 126 and the pressure of the gas within the gas chamber 120 act to return the flexible membrane 124 to its smooth, generally dome-shaped form, in which the circular opening of the exhalation port is occluded, and hence the exhalation port is closed. Although the flexible membrane 24 of the gas chamber component of FIGS. 4 to 7 will also close the exhalation port once the pressure of the exhaled gas within the exhalation port has dropped below the threshold pressure, the inclusion of the spring 126 reduces the time taken for this closure to take place. This reduction of time taken to close the exhalation port reduces the amount of breathing gas that escapes through the exhalation valve during closure, and hence increases the amount of breathing gas that is delivered to the patient.

Since deformation of the flexible membrane 124 from its generally planar, wrinkled form into a smooth, generally dome-shaped form does not involve overall stretching of the membrane 124, the spring constant of the spring 126 can be sufficiently small for the spring to offer only minimal resistance to the exhaled gas escaping through the exhalation port. The pressure of the gas within the gas chamber 120 is therefore in significantly closer agreement with the nominal patient end expiratory pressure applied to the respiratory circuit than has hitherto been possible with conventional exhalation valves.

What is claimed is:

1. An exhalation valve for use with an exhalation port of a respiratory circuit, the exhalation valve comprising:
   a hermetically sealed gas chamber,
   a gas inlet for supplying gas to the gas chamber, and
   a membrane of flexible material defining at least part of a wall of the gas chamber, the membrane being situated, in use, adjacent to the exhalation port, and the membrane being deformable by a change in the pressure differential between the gas within the gas chamber and the gas within the exhalation port between an inoperative configuration and an operative configuration in which the membrane restricts the flow of gas from the exhalation port to a greater extent than in said inoperative configuration, wherein the membrane is inherently planar but is sized and mounted within the exhalation valve such that the surface area of that part of the membrane that spans the space within which it is held is greater than the cross-sectional area of that space and deformation of the membrane to its operative configuration occurs substantially without increase of the surface area of the membrane.

2. An exhalation valve as claimed in claim 1, wherein the membrane completely occludes an exit opening of the exhalation port when in its operative configuration, and the surface area of that part of the membrane that occludes the exit opening is greater than the cross-sectional area of the exit opening.

3. An exhalation valve as claimed in claim 1, wherein the membrane is convoluted when in its inoperative configuration.

4. An exhalation valve as claimed in claim 3, wherein the convoluted form of the membrane is a form in which the membrane is disposed substantially in a plane, but with corrugations, furrows, wrinkles or ridges such that the membrane has peaks and troughs that extend either side of the plane.

5. An exhalation valve as claimed in claim 4, wherein the membrane adopts a more regular, generally dome-shaped, form on deformation to its operative configuration.

6. An exhalation valve as claimed in claim 1, wherein the operative configuration of the membrane either partially or completely occludes an exit opening of the exhalation port, and hence either partially or completely closes the exhalation port, and prevents or inhibits escape of a patient's exhaled breath, which is at a pressure below a threshold pressure, from the respiratory circuit, such that if the exhaled breath of the patient is at a pressure above the threshold pressure, the patient's exhaled breath deforms the membrane away from the exhalation port and escapes from the respiratory circuit.

7. An exhalation valve as claimed in claim 6, wherein the threshold pressure is substantially equivalent to the positive end expiratory pressure applied to the respiratory circuit at the exhalation port.

8. An exhalation valve as claimed in claim 7, wherein the exhalation valve is arranged such that the positive end expiratory pressure applied to the respiratory circuit at the exhalation port is substantially equal to the pressure of the gas within the gas chamber.

9. An exhalation valve as claimed in claim 1, wherein the exhalation valve is arranged such that before the gas inlet is connected to a supply of gas, and hence the pressure differential is zero, the membrane adopts its operative configuration.

10. An exhalation valve as claimed in claim 9, wherein the exhalation valve includes resilient means that bias the membrane towards its operative configuration.

11. An exhalation valve as claimed in claim 10, wherein the resilient means takes the form of a spring that is located within the gas chamber, and acts between the membrane and an opposing wall of the gas chamber.

12. An exhalation valve as claimed in claim 1, wherein the membrane is manufactured in an inherently smooth and planar form.

13. An exhalation valve as claimed in claim 12, wherein the membrane is a sheet of flexible material.

14. An exhalation valve as claimed in claim 13, wherein the gas chamber is defined by at least two cooperating components and the membrane of flexible material.

15. An exhalation valve as claimed in claim 14, wherein the two cooperating components are adapted to engage one another, and clamp the inherently planar membrane therebetween, along a closed and generally circumferential path.

16. An exhalation valve as claimed in claim 1, wherein the exhalation valve includes the exhalation port which is adapted to be connected, in fluid communication, to a respiratory circuit.

17. An exhalation valve as claimed in claim 16, wherein the exhalation valve includes a section of tubing that is adapted to be connected into a respiratory circuit, and the exhalation port branches from the section of tubing.

18. An exhalation valve as claimed in claim 16, wherein the exhalation port terminates at an exit opening through which exhaled breath from a patient escapes from the respiratory circuit.

19. An exhalation valve as claimed in claim 18, wherein the membrane is disposed parallel to, and above, the exit opening so that the operative configuration of the membrane occludes the exit opening completely.

20. A respiratory circuit including an exhalation valve as claimed in claim 1.

21. An exhalation valve for use with an exhalation port of a respiratory circuit, the exhalation valve comprising:
a hermetically sealed gas chamber,
a gas inlet for supplying gas to the gas chamber, and
a membrane of flexible material defining at least part of a wall of the gas chamber, the membrane being situated, in use, adjacent to the exhalation port, and the membrane being deformable by a change in the pressure differential between the gas within the gas chamber and the gas within the exhalation port between an inoperative configuration and an operative configuration in which the membrane restricts the flow of gas from the exhalation port to a greater extent than in said inoperative configuration, and resilient means that bias the membrane towards its operative configuration, wherein the membrane is inherently planar but is sized and mounted within the exhalation valve such that the surface area of that part of the membrane that spans the space within which it is held is greater than the cross-sectional area of that space and deformation of the membrane to its operative configuration occurs substantially without increase of the surface area of the membrane.

22. An exhalation valve as claimed in claim 21, wherein the membrane completely occludes an exit opening of the exhalation port when in its operative configuration, and the surface area of that part of the membrane that occludes the exit opening is greater than the cross-sectional area of the exit opening.

23. An exhalation valve as claimed in claim 21, wherein the membrane is convoluted when in its inoperative configuration.

24. An exhalation valve as claimed in claim 23, wherein the convoluted form of the membrane is a form in which the membrane is disposed substantially in a plane, but with corrugations, furrows, wrinkles or ridges such that the membrane has peaks and troughs that extend either side of the plane.

25. An exhalation valve as claimed in claim 24, wherein the membrane adopts a more regular, generally dome-shaped, form on deformation to its operative configuration.

26. An exhalation valve as claimed in claim 21, wherein the operative configuration of the membrane either partially or completely occludes an exit opening of the exhalation port, and hence either partially or completely closes the exhalation port, and prevents or inhibits escape of a patient's exhaled breath, which is at a pressure below a threshold pressure, from the respiratory circuit, such that if the exhaled breath of the patient is at a pressure above the threshold pressure, the patient's exhaled breath deforms the membrane away from the exhalation port and escapes from the respiratory circuit.

27. An exhalation valve as claimed in claim 26, wherein the threshold pressure is substantially equivalent to the positive end expiratory pressure applied to the respiratory circuit at the exhalation port.

28. An exhalation valve as claimed in claim 27, wherein the exhalation valve is arranged such that the positive end expiratory pressure applied to the respiratory circuit at the exhalation port is substantially equal to the pressure of the gas within the gas chamber.

29. An exhalation valve as claimed in claim 21, wherein the resilient means takes the form of a spring that is located within the gas chamber, and acts between the membrane and an opposing wall of the gas chamber.

30. An exhalation valve as claimed in claim 21, wherein the membrane is manufactured in an inherently smooth and planar form.

31. An exhalation valve as claimed in claim 30, wherein the membrane is a sheet of flexible material.

32. An exhalation valve as claimed in claim 31, wherein the gas chamber is defined by at least two cooperating components and the membrane of flexible material.

33. An exhalation valve as claimed in claim 32, wherein the two cooperating components are adapted to engage one another, and clamp the inherently planar membrane therebetween, along a closed and generally circumferential path.

34. An exhalation valve as claimed in claim 21, wherein the exhalation valve includes the exhalation port which is adapted to be connected, in fluid communication, to a respiratory circuit.

35. An exhalation valve as claimed in claim 34, wherein the exhalation valve includes a section of tubing that is adapted to be connected into a respiratory circuit, and the exhalation port branches from the section of tubing.

36. An exhalation valve as claimed in claim 34, wherein the exhalation port terminates at an exit opening through which exhaled breath from a patient escapes from the respiratory circuit.

37. An exhalation valve as claimed in claim 36, wherein the membrane is disposed parallel to, and above, the exit opening so that the operative configuration of the membrane occludes the exit opening completely.

* * * * *